United States Patent [19]

Erbeck

[11] Patent Number: 5,128,550
[45] Date of Patent: Jul. 7, 1992

[54] METHOD OF AND AN APPARATUS FOR TESTING LARGE AREA PANES FOR OPTICAL QUALITY

[75] Inventor: Ralf Erbeck, Hattingen, Fed. Rep. of Germany

[73] Assignee: Flachgas Aktiengesellschaft, Fürth, Fed. Rep. of Germany

[21] Appl. No.: 572,184

[22] Filed: Aug. 23, 1990

[30] Foreign Application Priority Data

Sep. 2, 1989 [DE] Fed. Rep. of Germany ....... 3929234
Nov. 11, 1989 [DE] Fed. Rep. of Germany ....... 3937559

[51] Int. Cl.$^5$ .............................................. G01N 21/88
[52] U.S. Cl. ..................................... 250/572; 356/374
[58] Field of Search ............... 250/571, 572; 356/374, 356/397, 376, 239, 240

[56] References Cited

U.S. PATENT DOCUMENTS

| 3,166,627 | 1/1965 | Shaw, Jr. .............................. 356/239 |
| 4,459,027 | 7/1984 | Kafri ...................................... 356/128 |
| 4,939,380 | 7/1990 | Berger et al. ......................... 356/374 |

FOREIGN PATENT DOCUMENTS 3600199 7/1986 Fed. Rep. of Germany.
52103443 3/1979 Japan .................................. 356/374

OTHER PUBLICATIONS

J. Sci. Instrum., vol. 42, pp. 607–610, "Slope measurement by means of moire fringes", by P. S. Theocars et al. (May 1965).

Optik, vol. 72, No. 3, pp. 115-119 "Das Phasenschiftverfahren zur Moire-Bildauswertung" by K. Anersen (Jul. 1985).

Primary Examiner—David C. Nelms
Assistant Examiner—Que T. Le
Attorney, Agent, or Firm—Herbert Dubno

[57] ABSTRACT

A method of testing large area panes of a transparent material for optical quality, especially automotive windshield, uses a light box having a uniformly illuminated wall along which a planar grating is provided. The grating has an area at least equal to that of the windshield which is spaced from that gravity. An objective in line with the windshield and the grating forms an image of the grating through the windshield on a plane having a reference grating of much smaller size to form a Moiré-pattern superposition which is picked up by a video camera and subjected to phase shift analysis.

15 Claims, 1 Drawing Sheet

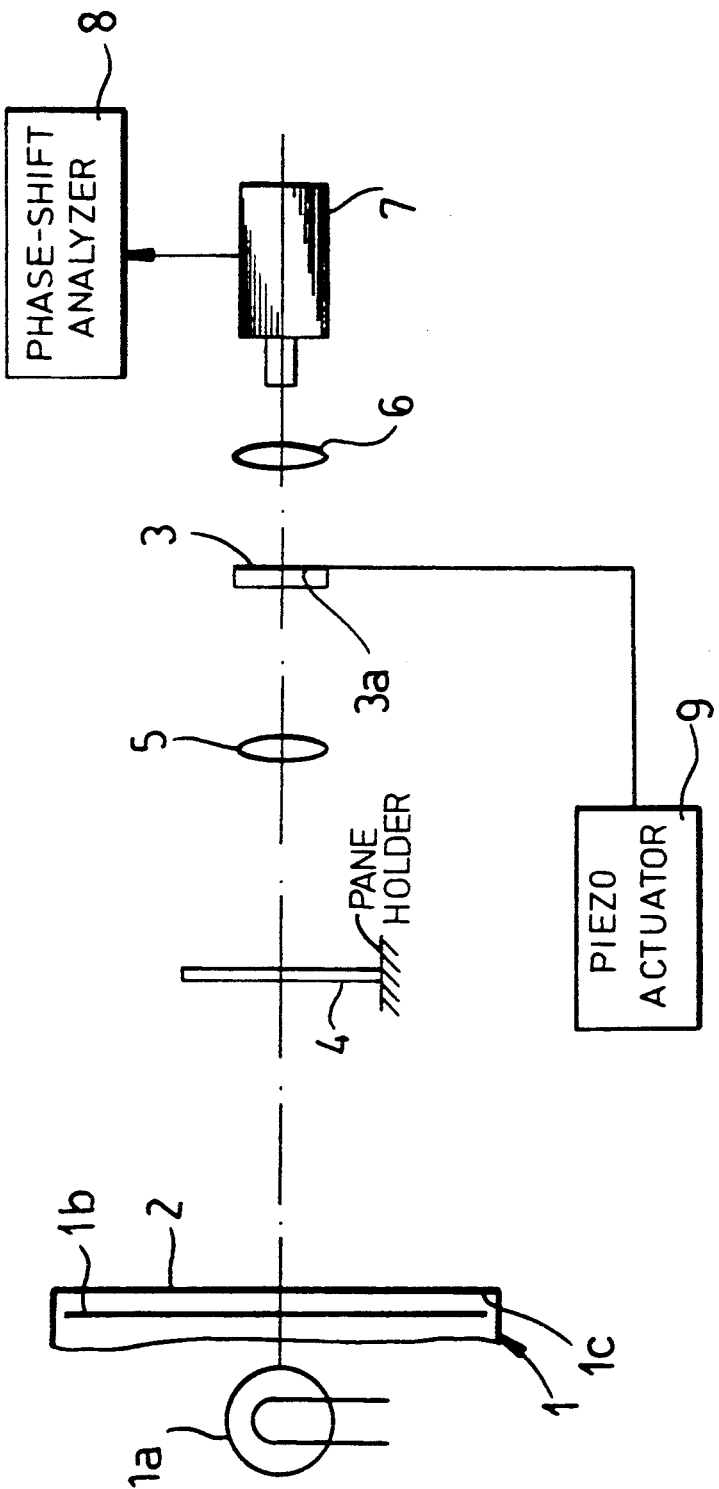

METHOD OF AND AN APPARATUS FOR TESTING LARGE AREA PANES FOR OPTICAL QUALITY

FIELD OF THE INVENTION

My present invention relates to a method of and to an apparatus for the testing of large-area panes of a transparent material such as glass, especially motor vehicle windshields, for optical quality.

The testing of optical quality in accordance with the invention utilizes the principle of Moiré image or pattern evaluation, the Moiré pattern being formed by the superposition of a transluminated planar or flat grating projected by an objective on a reference grating so that the Moiré image can be referred to as a Moiré-pattern superposition defined by the image of the planar grating on the reference grating.

The reference to large-area panes is intended to mean panes the size of conventional window panes and especially motor vehicle window panes, specifically intending thereby automobile windshields.

The term "planar grating" is used herein to describe a grating which can be applied to a surface, for example, a surface of a glass plate, or a transparent foil. Various grating geometries can be used and it will be understood that the reference grating should be geometrically similarly with the planar grating and, indeed, should exactly correspond to the planar grating although it is of reduced scale, depending upon the reduction effected by the objective as will be described in greater detail below.

BACKGROUND OF THE INVENTION

Moiré-pattern evaluation in which a transluminated planar grating is projected by an objective upon a reference grating so that the Moiré-pattern is formed as the superposition of the image of the flat grating and the reference grating is described in *J. Sci. Instrum.*, Vol. 42, P. 607 to 610, although this system is not used for testing optical quality of large area transparent vehicle windshields which are mass produced or produced in serial production systems in the context of a more or less automatic fabrication process. This known Moiré pattern evaluation as described in this publication serves a purely scientific purpose with respect to detecting small irregularities of small transparent plates with an area of several square centimeters.

In this system, monochromatic light is transmitted as a bundle of parallel light pencils or rays with the aid of special optics onto the planar grating and transluminates the latter. These optics, the planar grating, the plate whose irregularities are to be detected, the objective and the reference grating have more or less the same size. The reference grating in particular is not significantly smaller than the planar grating or the plate whose irregularities are to be detected.

There is no teaching in the reference whatever as to how this system might be employed in the optical testing of large area panes and a simple upscaling of this earlier system for automotive windshield optical testing would lead to an extremely expensive apparatus because it would require optical devices of large diameter which are costly to fabricate, especially if they are to have the desired precision and resolution.

There is, however, a method known for the qualitative optical testing of automotive glass panes, especially automobile windshields (see German Open Application DE-OS 3600199) which uses a planar grating in the form of a transparency slide or diapositive. This grating is projected with the aid of a projector upon a projection surface on which the reference grating is provided. An objective in this case is provided in the projector. The windshield to be subjected to optical testing is in the projection path, i.e. in the path of the light rays between the objection of the projector and the projection surface.

The measurement signal is obtained in the form of a refractive power deviation in the presence of an optical defect in the vehicle pane which results from a distortion of the projective grating by comparison with the projected grating and the pattern obtained in the absence of the optical defect.

This system has the disadvantage that visual inspection is required and this, of course, requires appropriate personnel. A measurement value can be obtained only in the center of a Moiré strip at which poor resolution results. The refractive power is determined from the inclination of the Moiré lines. The image quality of the Moiré-pattern is poor because of a poor contrast arising from the fact that sharply projected grating lines are not fully absorbed on the darker regions of the projection wall or surface. In the superposition of two clear lines on the projection surface, the backscattered light intensity is substantially smaller than in the case of a transmission. The socalled shadow image which results in addition to the Moiré pattern is superimposed upon it and tends to obscure the Moiré pattern so that in some cases at least the Moiré pattern is simply not capable of practical evaluation.

The processing of the Moiré pattern in this conventional system is effected by electrical image processing in a strip sequence scanning which excludes efficient parallel computation process from being employed. As a consequence, the process time per measurement is comparatively high.

The determination of the inclination of the Moiré strips cannot be reliably effected by this earlier system and thus the resolution of the system can require improvement. As a consequence, problems are encountered if this earlier windshield optical testing method is to satisfy the requirements of German Industrial Standard DIN 52 305 or ECE 43 which must be satisfied by the present invention.

OBJECTS OF THE INVENTION

It is, therefore, the principal object of the present invention to provide an improved method for the optical quality testing of mass produced large area panes, such as automotive windshields, whereby drawbacks of the prior art methods described above can be avoided.

Another object of the invention is to provide a method for the process described which affords optical quality testing of large area glass panes with high sensitivity, precision and resolution power.

It is also an object of the invention to provide a relatively simple method of determining optical quality in large area glass panes with electronic evaluation of a Moiré pattern whereby the evaluation can be effected in an extremely short time span.

Still another object of the invention is to provide an improved apparatus for carrying out the method of the invention.

SUMMARY OF THE INVENTION

These objects and others which will become apparent hereinafter are attained in a method of testing large-area panes of a transparent material which comprises the steps of:

(a) illuminating a planar grating on a uniformly illuminated surface having an area at least equal to that of a large-area pane of the transparent material to be tested for optical quality and disposed at one side of the large-area pane;

(b) collecting light from the surface transluminating the large-area pane with an objective and superposing with the light collected by the objective an image of the planar grating transmitted through the large-area pane upon a reference grating having an area which is only a fraction of the area of the large-area pane thereby forming a Moiré-pattern superposition of the image of the planar grating with the reference grating; and (c) picking up the Moiré-pattern superposition with a video camera and subjecting the Moiré-pattern superposition picked up by the video camera to a phase shift analysis using as a measure of refracting power a brightness distribution of a picture of the Moiré-pattern superposition taken by the video camera, thereby producing an output representing overall optical quality of the large-area pane.

According to the invention, the process for testing the optical quality of large area panes of a transparent material such as glass, especially automobile windshields, utilizes a Moiré pattern evaluation in which a transluminated flat grating is imaged on a reference grating through an objective so that the Moiré pattern is a superposition of the image of the flat grating and the reference grating According to the invention the flat grating is provided on a back-illuminated, uniformly transluminated light wall which has an area or size at least equal to that of the automobile windshield to be tested.

The automobile windshield to be tested is disposed between the flat grating and the objective which images the flat grating upon the reference grating. The reference grating has an area or size which is a fraction of the area or size of the automobile windshield to be tested.

The superimposed image is picked up, according to the invention, by a video camera and is subjected to a phase shift analysis processing with the measure of the resolving power being determined by the brightness distribution picked up by the video camera.

It will be self understood that the light wall or light box which, from the point of view of the objective, is located behind the automotive pane to be tested, should be at least coextensive in area with the of the pane.

In the system of the invention, the reference grating is transluminated.

In accordance with the principles of the invention, the video camera is focused sharply upon the superimposed image further at the reference grating. It is possible that a socalled shadow image of the pane to be tested will be cast upon the superposition image. In that case, the video camera can be so adjusted that the shadow image of the pane to be tested does not detrimentally affect the image picked up by the video camera.

It is also possible, in accordance with the invention to focus the video camera sharply upon the image plane of the automobile windshield With this setting, for example, the holders of the pane may appear sharply in the image of the video camera. Even in this case there is sufficient depth of field to allow evaluation of the Moiré superposition image.

The phase shift process which is employed, i.e. the phase shift analysis, can be that which has been described for a entire differently process, in the publication "Optik" (1980), P 115-119, Wissenschaftliche Verlagsgesellschaft mbH. Stuttgart.

This type of processing permits a fully automatic analysis of the Moiré patterns in which, for example, the local grating distortions are calculated in terms of gray value intersticies of a plurality, e.g. three Moiré patterns which are generated. To evaluate the required number three of Moiré patterns, a shift of the reference grating and flat grating is effected. This shift is effected perpendicularly to the grating lines and can be effected, for example, by means of a piezo actuator.

In the imaging of the flat grating with aid of the objective on the reference grating through the automobile windshield to be tested and which may have refractive power variations, the imaged flat grate lines differ in accordance with the refractive power fluctuations as a fluctuation of the coordinates of the flat grating, shifted by the quality $\Delta s$. Where the magnitude $\Delta s$ is constant, the refractive power is zero. With the phase shift process for analyzing the Moiré patterns, this $\Delta s$ can be measured and displayed.

According to a feature of the invention, the pane to be tested is spaced from the light wall by a distance at least equal to the largest dimension of the pane, i.e. its greatest linear dimension or extension. In the case of an automotive vehicle windshield for a conventional vehicle, this distance is about 2 meters or more.

The distance between the pane and the objective probably is between 8 and 10 meters and most advantageously can be about 9 meters.

The light wall is, as described, back illuminated uniformly.

This can be accomplished by providing this wall with a light scattering plate.

In a preferred embodiment, the flat grating is imaged on a reference grating whose area is only several square centimeters. For example, I can use a flat grating whose grating constant is 0.25 to 3 lines /mm, preferably about one line /mm. The reference grating, then, can have a grating constant of about 10 to 80 lines /mm, preferably about 40 lines /mm.

The indicated line densities can be made without significant cost and give especially effective results. The optical reduction thus will range between 20:1 and 80:1 and preferably is about 40:1.

In principle, the method of the invention can be practiced using basically any video camera. However, the resolving power is also determined by the resolution of the video camera. Thus it is preferred to employ a video camera which has a resolution such that it is greater than the test precision and the parameters and requirements for such a camera are selected so that they do not reduce the test precision below the minimum acceptable.

The resolution in the horizontal and vertical directions should correspond, therefore to the resolution of the subsequent image processing steps. Advantageously no special illumination is required for the video camera so that the video camera can be used to measure the brightness distribution of the picked up image. The number of pixels /mm need not be a multiple of the raster constant to prevent detrimental Moiré effects between the chips of the video camera and the superposition image.

In general, best results are obtained where superflat grating and reference grating are close gratings or gridtype gratings. In a preferred embodiment of the invention, upstream of the reference grating and the plane at which the superposition image is formed, a field lens is provided. It is possible according to the invention as well to provide a matte-finish optical plate along the side of the superposition image opposite that at which the camera is provided and indeed to form the reference grating upon such plate.

BRIEF DESCRIPTION OF THE DRAWING

The above and other objects, features and advantages of my invention will become more readily apparent from the following description, reference being made to the accompanying highly diagrammatic drawing, the sole FIGURE of which is a diagram of an apparatus for carrying out the method of the invention.

SPECIFIC DESCRIPTION

I have shown a light box generally represented at 1 which can comprise a light source 1a and a light-diffusing glass plate 1b which serves to transluminate uniformly a light wall 1c on which is provided a flat grating, this wall and grating having an area at least equal to the area of a large-area glass pane represented at 4, such as an automotive windshield, to be subjected to optical quality testing.

A reference flat grating 3 is provided on a matte-finish optical diffusing glass plate, such as a ground-glass plate 3a at a substantial spacing as described from the grating 2.

Thus, between the grating 2 and 3, the glass pane 4 to be subjected to the optical testing is disposed.

Also between these gratings and, specifically, between the glass pane 4 and the grating 3 an objective system represented by the collecting lens 5 is shown, the lens 5 focusing the image of the grating 2 through the pane 3 upon an image plane corresponding to the plane of the reference grating 3.

Stated otherwise, the apparatus is so set up that the image of the grating 2 generated by the objective 5 on the reference grating 3 forms a Moiré pattern superimposed in this plane. The image can be picked up, in addition, by a field lens 6 which is located ahead of the superposition image with respect to the video camera. The video camera 7 picks up the superposition image and this image is submitted to phase shift analysis in the unit 8 in accordance with the method described in "Optik" (1980), P 115-119, Wissenschaftliche Verlagsgesellschaft mbH, Stuttgart.

The shifting of the gratings is effected by the piezo actuator 9 also represented diagrammatically in the drawing.

We claim:

1. A method of testing large-area panes of a transparent material for optical refraction quality, comprising the steps of:
    (a) illuminating a planar grating on a uniformly illuminated surface having an area at least equal to that of a large-area pane of said transparent material to be tested for optical quality and disposed at one side of said large-area pane;
    (b) collecting light from said surface transluminating said large-area pane with an objective lens system and directing the light collected by said objective and forming an image of said planar grating transmitted through said large-area pane upon a reference grating having an area which is only a fraction of the area of said large-area pane thereby forming a Moiré-pattern superposition of the image of said planar grating with said reference grating; and
    (c) picking up said Moiré-pattern superposition with a video camera and subjecting the Moiré-pattern superposition picked up by said video camera to a phase shift analysis using as a measure of refracting power a brightness distribution of a picture of said Moiré-pattern superposition taken by said video camera, thereby producing an output representing optical refractivity of said large-area pane.

2. The method defined in claim 1 wherein said planar grating is imaged upon said reference grating in step (b) which has an area of only several square centimeters.

3. The method defined in claim 1 wherein said planar grating has a grating constant of 0.25 to 2 lines /mm.

4. The method defined in claim 3 wherein said grating constant is about 1 line /mm.

5. The method defined in claim 3 wherein said reference grating has a grating constant of 10 to 80 lines /mm.

6. The method defined in claim 5 wherein said grating constant of said reference grating is about 40 lines /mm 7. The method defined in claim 1 wherein said video camera is focused sharply upon said Moiré-pattern superposition 8. The method defined in claim 1 wherein said video camera is focused sharply upon an image plane of said pane.

9. The method defined in claim 1 wherein said gratings are grids.

10. The method defined in claim 1 wherein said objective forms an optical reducer with a ratio of 20:1 to 80:1.

11. The method defined in claim 10 wherein said ratio is about 40:1.

12. The method defined in claim 1 wherein said Moiré-pattern superposition is formed through a field lens ahead of said superposition.

13. The method defined in claim 1 wherein said Moiré-pattern superposition is formed through a matte-finish optical plate.

14. The method defined in claim 13 wherein said reference grating is applied to said matte-finish optical plate.

15. An apparatus for testing large-area panes of a transparent material for optical quality by refractivity analysis, comprising:
    a light box having a uniformly illuminated light wall of an area at least equal to that of a large-area pane to be tested;
    a planar grating on said wall extending over said area;
    means for supporting said large-area pane at a distance from said planar grating at least equal to a maximum linear dimension of said large-area pane;
    an objective lens spaced from said large area pane and forming an image of said planar grating through said large area pane on an image plane spaced from said objective;
    a reference grating in said plane having an area less than the area of said pane and generating a Moiré pattern superposition of said image on said reference grating;
    a video camera trained on said plane for picking up said Moiré pattern superposition; and
    means connected to said video camera for subjecting the Moiré pattern superposition picked up by said video camera to phase shift analysis, thereby providing an output indicating optical refractivity of said pane.

* * * * *